(12) United States Patent
Chen et al.

(10) Patent No.: US 10,510,145 B2
(45) Date of Patent: Dec. 17, 2019

(54) MEDICAL IMAGE COMPARISON METHOD AND SYSTEM THEREOF

(71) Applicant: INDUSTRIAL TECHNOLOGY RESEARCH INSTITUTE, Hsin-Chu (TW)

(72) Inventors: Jian-Ren Chen, Hsinchu (TW); Guan-An Chen, Hsinchu (TW); Su-Chen Huang, Taoyuan (TW); Yue-Min Jiang, New Taipei (TW)

(73) Assignee: INDUSTRIAL TECHNOLOGY RESEARCH INSTITUTE, Hsin-Chu (TW)

( * ) Notice: Subject to any disclaimer, the term of this patent is extended or adjusted under 35 U.S.C. 154(b) by 100 days.

(21) Appl. No.: 15/855,082

(22) Filed: Dec. 27, 2017

(65) Prior Publication Data

US 2019/0197689 A1    Jun. 27, 2019

(51) Int. Cl.
*G06T 7/00* (2017.01)
*G06K 9/62* (2006.01)
(Continued)

(52) U.S. Cl.
CPC .......... *G06T 7/0016* (2013.01); *A61B 3/0025* (2013.01); *A61B 3/1241* (2013.01);
(Continued)

(58) Field of Classification Search
CPC .. G06K 9/2054; G06K 9/4671; G06K 9/6202; G06K 9/6218; A61B 3/0025; A61B 3/1241; A61B 3/145
See application file for complete search history.

(56) References Cited

U.S. PATENT DOCUMENTS 7,856,135 B1    12/2010 Bernardes
2015/0110348 A1    4/2015 Solanki et al.
(Continued)

FOREIGN PATENT DOCUMENTS

CN    100530220 C    8/2009
CN    106846317 A    6/2017
(Continued)

OTHER PUBLICATIONS

Taiwan Patent Office, "Office Action", dated Sep. 3, 2018, Taiwan.
(Continued)

*Primary Examiner* — Leon Flores
(74) *Attorney, Agent, or Firm* — Locke Lord LLP; Tim Tingkang Xia, Esq.

(57) ABSTRACT

A medical image comparison method is firstly to obtain plural images of the same body at different time points. Then, obtain a first feature point group by detecting feature points in the first image captured at a first time point, and a second feature point group by identifying feature points in the second image captured at a second time point. An overlapping image information is generated by aligning the second image with the first image according to the first and second feature point groups. Then, window areas corresponding to a first matching image and a second matching image of the overlapping image information are extracted one by one by sliding a window mask, and an image difference ratio for each of the window areas is calculated. In addition, a medical image comparison system is also provided.

15 Claims, 10 Drawing Sheets

(51) Int. Cl.
*G06K 9/46* (2006.01)
*G06T 7/33* (2017.01)
*G06K 9/20* (2006.01)
*G06T 7/11* (2017.01)
*A61B 3/00* (2006.01)
*A61B 3/14* (2006.01)
*A61B 3/12* (2006.01)

(52) U.S. Cl.
CPC ............ *A61B 3/145* (2013.01); *G06K 9/2054* (2013.01); *G06K 9/4671* (2013.01); *G06K 9/6202* (2013.01); *G06K 9/6218* (2013.01); *G06T 7/11* (2017.01); *G06T 7/337* (2017.01); *G06T 2207/30041* (2013.01)

(56) References Cited

U.S. PATENT DOCUMENTS

2016/0012311 A1* 1/2016 Romanik ............ G06K 9/6203
   382/201
2016/0078622 A1 3/2016 Hsiao et al.
2017/0055814 A1* 3/2017 Wang ................ A61B 1/00009
2017/0076145 A1 3/2017 Gottemukkula et al.

FOREIGN PATENT DOCUMENTS

| TW | 201225003 A | 6/2012 |
| TW | 201250608 A | 12/2012 |
| TW | I452998 B | 9/2014 |
| TW | I1459821 B | 11/2014 |
| TW | 201509363 A | 3/2015 |
| TW | M528483 | 9/2016 |
| TW | I579173 B | 4/2017 |

OTHER PUBLICATIONS

Satoshi Sakuma et al., Automated detection of changes in sequential color ocular fundus images. Part of the SPIE Conference on Image processing, 1998, vol. 3338.

* cited by examiner

MEDICAL IMAGE COMPARISON METHOD AND SYSTEM THEREOF

TECHNICAL FIELD

The present disclosure relates to a medical image comparison method and system thereof, and more particularly, to medical image comparison method and system for assisting medical doctors to do medical diagnosis.

BACKGROUND

With rapid advance in medical image diagnosis, medical personnel is becoming more and more accustomed to use medical imaging as an assisting means for diagnosing the clinical condition of a patient, and thereby, minute pathological changes in living organisms can be detected before the appearance of symptoms.

Retinal examination is a diagnostic procedure that allows the ophthalmologist to obtain a better view of the retinal of you eye and to look for signs of eye disease such as retinal detachment, optic neuritis, macular degeneration, glaucoma and other retinal issues. It is noted that eye is the only organ whose nerves can be detected in a non-invasive manner, and thus generally it can be treated as a microcosm of all the important organs in our body. Therefore, retinal images not only can be used by ophthalmologist for diagnosing eye diseases, but also clinically it can reveal representative pathological changes of organs other than eyes. That is, physicians of other disciplines, such as metabolism or neurology, can use retinal images for detecting early pathological changes of other diseases, such as diabetes, high blood pressure, high blood cholesterol, auto immune disease, etc.

For those conventional medical imaging techniques that are currently available, such as the aforesaid fundus imaging, patients have to be subjected to an retinal examination once every two years for tracking the morphology of a target area. However, since there may be differences in imaging angle, the use of light source, luminance and parameter configuration between different retinal imaging processes, the resulted retinal images are different accordingly. Thus, physicians have to manually search and find all the differences between retinal images that are taken at different time, which not only it is a time-consuming and labor-intensive task, but also the manual difference identification may easily leads to misdiagnosis as human error is not a easy task to prevent. Moreover, owing to the subjective valuation difference, different physicians may have different identification results about the same retinal image.

Therefore, it is in need of an improved medical image comparison method and system thereof, capable of overcoming the aforesaid problems.

SUMMARY

The present disclosure provides a medical image comparison method and system, which can be used for allowing a physician to compare medical images of a specific area in a patient that are taken at different time so as to locate a region of variation from the medical images, and thus for assisting the physicians to do medical diagnosis.

In an embodiment, the present disclosure provides a medical image comparison method, which comprises the steps of: obtaining a plurality of images of a body at different time points, while allowing the plural images to include a first image captured at a first time point and a second image captured at a second time point; obtaining a first feature point group by detecting feature points in the first image, while obtaining a second feature point group by detecting feature points in the second image; enabling an overlapping image information to be generated by aligning the second image with the first image according to the first feature point group and the second feature point group, while allowing the overlapping image information to include a first matching image corresponding to the first image and a second matching image corresponding to the second image; and sequentially extracting corresponding window areas from the first matching image and the second matching image in the overlapping image information respectively by the use of a sliding window mask, while calculating an image difference ratio for each of the window areas according to the ratio between the number of matching points and the number of unmatched points in the corresponding window areas of the first and the second matching images.

In an embodiment, the present disclosure provides a medical image comparison system, which comprises: an image processing device and an image calculation device. The image processing device further comprises: an image capturing module, a feature extracting module and an information alignment module. The image capturing module is used for obtaining a plurality of images of a body at different time points, while allowing the plural images to include a first image captured at a first time point and a second image captured at a second time point. The feature extracting module is used for obtaining a first feature point group by detecting feature points in the first image, while obtaining a second feature point group by detecting feature points in the second image. The image alignment module is coupled to the feature extracting module and is used for aligning the second image with the first image according to the first feature point group and the second feature point group so as to generate an overlapping image information, whereas the overlapping image information includes a first matching image corresponding to the first image and a second matching image corresponding to the second image. The image calculation device, that is coupled to the image processing device, further comprises: a difference comparison module, provided for sequentially extracting corresponding window areas from the first matching image and the second matching image in the overlapping image information respectively by the use of a sliding window mask, while calculating an image difference ratio for each of the window areas according to the ratio between the number of matching points and the number of unmatched points in the corresponding window areas of the first and the second matching images.

From the above description, the medical comparison method and system of the present disclosure are capable of rapidly comparing medical images of a specific area in a patient that are taken at different time according to the image difference ratio so as to locate a region of variation from the medical images, by that physicians not only can be relieved from the time-consuming and labor-intensive task of having to manually search and find all the differences between retinal images that are taken at different time, but also from possible misdiagnosis caused by human error. Moreover, physicians are enabled to make a more objective valuation to determine whether or not the region of variation is an indication of deterioration for assisting the physicians to arrange corresponding tracking procedures.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
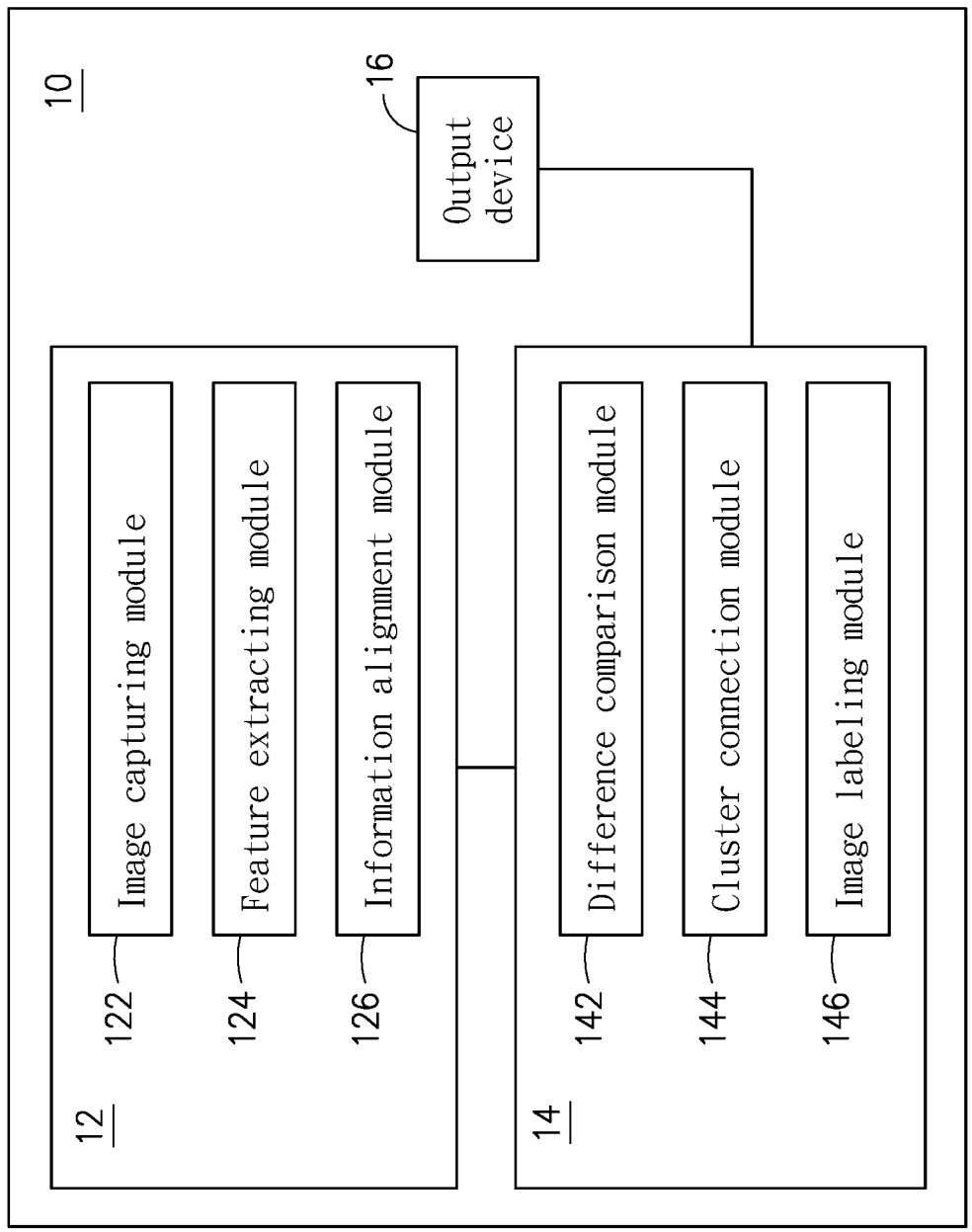
FIG. 1 is a schematic diagram showing a medical image comparison system according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1 is a schematic diagram showing a medical image comparison system according to an embodiment of the present disclosure. In FIG. 1, an exemplified medical image comparison system is disclosed, which comprises: an image processing device 12, an image calculation device 14 and an output device 16.

In this embodiment, the image processing device 12 is used for performing a series of image processing procedures on images of an object that are captured at different time points, including import images, feature extraction, feature points matching, and image alignment, so as to obtain a correlated image area of the images to be used as a region of interest (ROI) for analysis.

In detail, the image processing device further comprises: an image capturing module 122, a feature extracting module 124 and an information alignment module 126.

In this embodiment, the image capturing module 122 can be any electronic device with imaging capability, such as a camcorder with one or more CCD/CMOS, but it is not limited thereby. In one embodiment, the image capturing module 122 can be an image information transceiver interface that is used for receiving image information from other imaging unit or for transmitting image information to other units.

The image capturing module 122 is provided for capturing images of an object to be detected, which can be a body part of a user, while the images to be captured can be a map of vein network depicting blood vessel caliber, crotch angle and vessel angulation. In an embodiment, the image capturing module 122 is an eye exam device to be used for capturing image of eyes of a body so as to obtain corresponding retinal images.

In this embodiment, the feature extracting module 124 can be a hardware, e.g. an integrated circuit, a software, e.g. a program, or the combination of the two. The feature extracting module 124 is coupled to the image capturing module 122 for receiving images from the image capturing module 122 to be used for detecting feature points in the received image.

In this embodiment, the image calculation device 14 can be a hardware, e.g. an integrated circuit, a software, e.g. a program, or the combination of the two. The image calculation device 14 is coupled to the image processing device 12 for receiving the overlapping image information from the information alignment module 126 of the image processing device 12. The image calculation device 14 is provided enabled to perform a series of image processing procedures on the overlapping image information for detecting and calculating image difference ratios of window areas defined in the overlapping image information while clustering the window areas according to their correlation that is determined based upon the image difference ratios, and thus labeling an ROI as a region of variation.

In detail, the image calculation device 14 further comprises: a difference comparison module 142, a cluster connection module 144, and an image labeling module 146.

In this embodiment, the difference comparison module 142 uses a sliding window mask to sequentially extract corresponding window areas from two images in the overlapping image information and then calculating an image difference ratio for each of the window areas according to the ratio between the number of matching points and the number of unmatched points in the corresponding window areas.

In this embodiment, the cluster connection module 144 is coupled to the difference comparison module 142, which is performed based upon a connecting component labeling algorithm for clustering the connectivity of the window areas in the overlapping image information according to the image difference ratio of each of the window areas.

In this embodiment, the image labeling module 146 is coupled to the cluster connection module 144, which is provided for labeling an ROI as a region of variation according to the connectivity of the window areas in the overlapping image information.

In this embodiment, the output device 16 is coupled to the image calculation device 14 for outputting the labeled region of variation of the overlapping image information, The output device 16 can be a display panel that is provided for displaying the labeled region of variation graphically for assisting the physicians to do medical diagnosis. Nevertheless, the output device 16 is not limited thereby, and in other embodiments, the labeled region of variation can be outputted and presented by sounds, characters, lighting, and so on.

Figure 2:
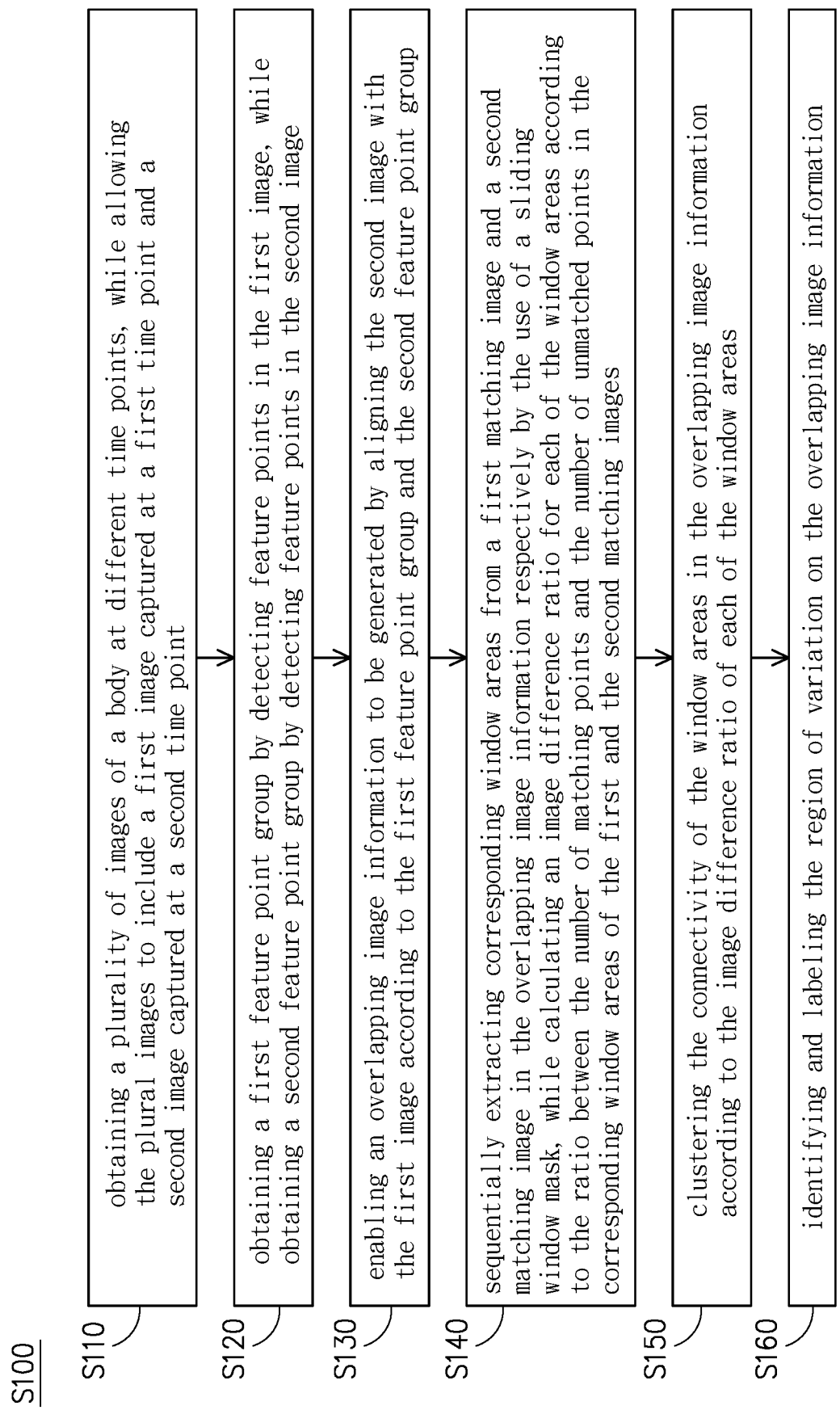
FIG. 2 is a flow chart depicting steps performed in a medical image comparison method according to an embodiment of the present disclosure.

FIG. 2 is a flow chart depicting steps performed in a medical image comparison method according to an embodiment of the present disclosure. The medical image comparison method S100 of FIG. 2 is adapted for the medical image comparison system 10 of FIG. 1.

In this embodiment, the medical image comparison method S100 includes the step S110 to step S160.

At step S110, a plurality of images of a body at different time points are obtained, whereas the plural images include a first image captured at a first time point and a second image captured at a second time point.

Figure 3B:
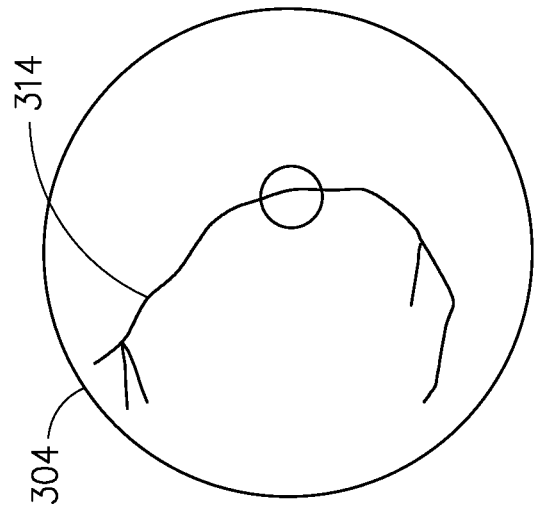
FIG. 3B is a schematic diagram showing another retinal image of the same eye of FIG. 3A that is captured at a second time point.
Figure 3A:
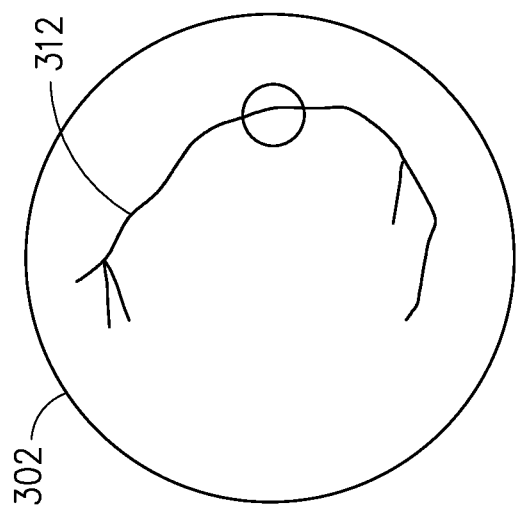
FIG. 3A is a schematic diagram showing a retinal image of an eye that is captured at a first time point according to an embodiment of the present disclosure.

In an embodiment, the first time point and the second time point are not set to be the same, according to that the first image is an image captured earlier to be used as a reference image, while the second image is an image captured later in time to be used as a comparison image. In addition, the two images of the body that are captured at different time points can be any two images of the same body that only have to be captured earlier and later in time, but without being limited by shooting angle, luminance, contrast, saturation and sharpness. FIG. 3A is a schematic diagram showing a retinal image of an eye that is captured at a first time point according to an embodiment of the present disclosure. FIG. 3B is a schematic diagram showing another retinal image of the same eye of FIG. 3A that is captured at a second time point. In this embodiment, the image capturing module 122 is enabled to capture retinal images on the same eye of a body at different time points. As shown in FIG. 3A, the first image 302 that is captured at a first time point includes a first blood vessel 312; and as shown in FIG. 3B, the second image 304 that is captured at a second time point includes a second blood vessel 314. Comparing with the positioning of the first blood vessel 312 in the first image 302, the position of the second vessel 314 in the second image 304 is shifted.

At step S120, with reference to FIG. 2, a first feature point group is obtained by detecting feature points in the first image, and a second feature point group is obtained by detecting feature points in the second image. It is noted that the feature points can be the singular points detected in the color space or illumination space of the images.

Figure 4B:
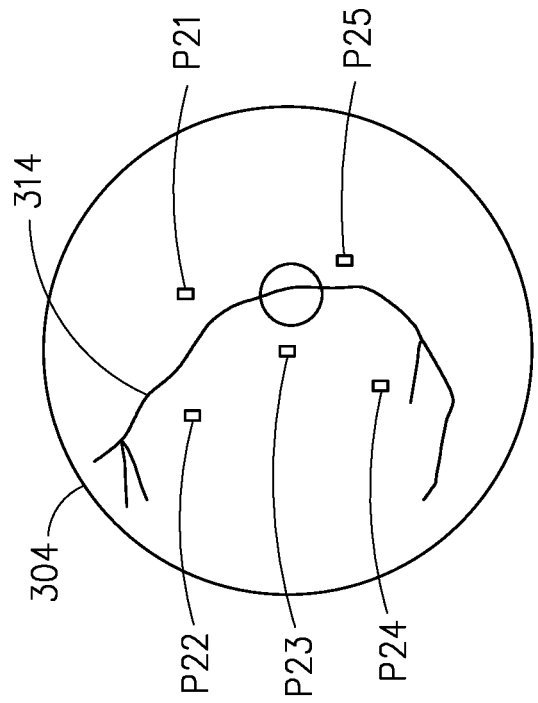
FIG. 4B is a schematic diagram showing feature points detected from the second image of FIG. 3B.
Figure 4A:
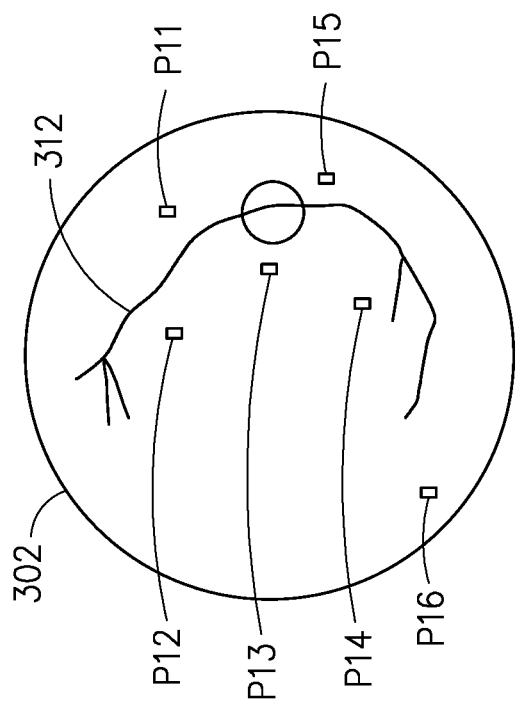
FIG. 4A is a schematic diagram showing feature points detected from the first image of FIG. 3A.

In this embodiment, the feature extracting module 124 uses image feature extraction techniques, such as the scale invariant feature transform (SIFT) algorithm and the speeded-up robust features (SURF) algorithm, to obtain the first feature point group of the first image and the second feature point group of the second image. FIG. 4A is a schematic diagram showing feature points detected from the first image of FIG. 3A. FIG. 4B is a schematic diagram showing feature points detected from the second image of FIG. 3B. As the embodiment shown in FIG. 4A, the feature extracting module 124 uses the aforesaid image feature extraction techniques to obtain the feature points P11~P16 of the first image 302 and the feature points P21~P25 of the second image 301, which are defined respectively as the first feature point group and the second feature point group. In this embodiment, the feature points P11~P15 match to the feature points P21~P25 in an one-on-one manner, while leaving the feature point P16 to stand along without matching point to be found in the second image 304. However, the present disclosure is not limited by the aforesaid embodiment.

Figure 5B:
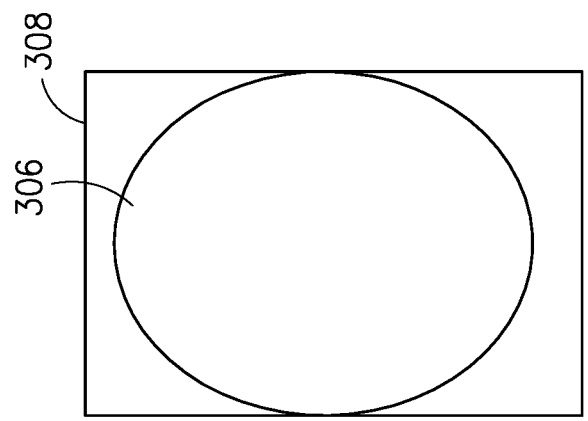
FIG. 5B is a schematic diagram showing an overlapping image information extracted FIG. 5A.
Figure 5A:
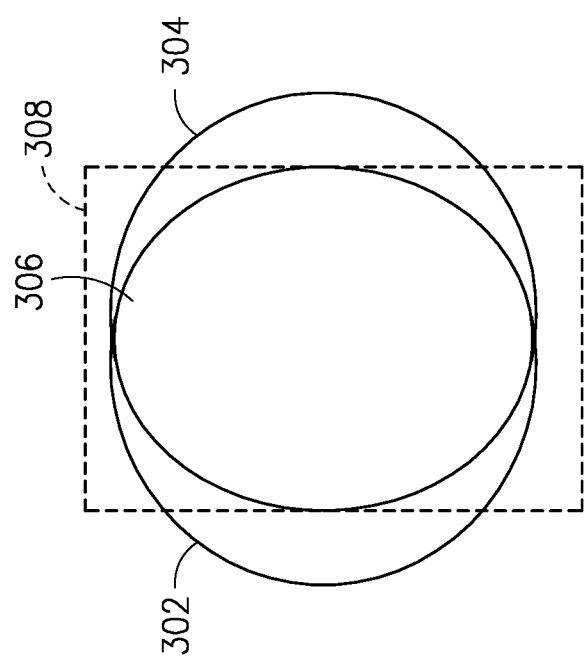
FIG. 5A is a schematic diagram showing the aligning of the second image to the first image according to an embodiment of the present disclosure.
Figure 6:
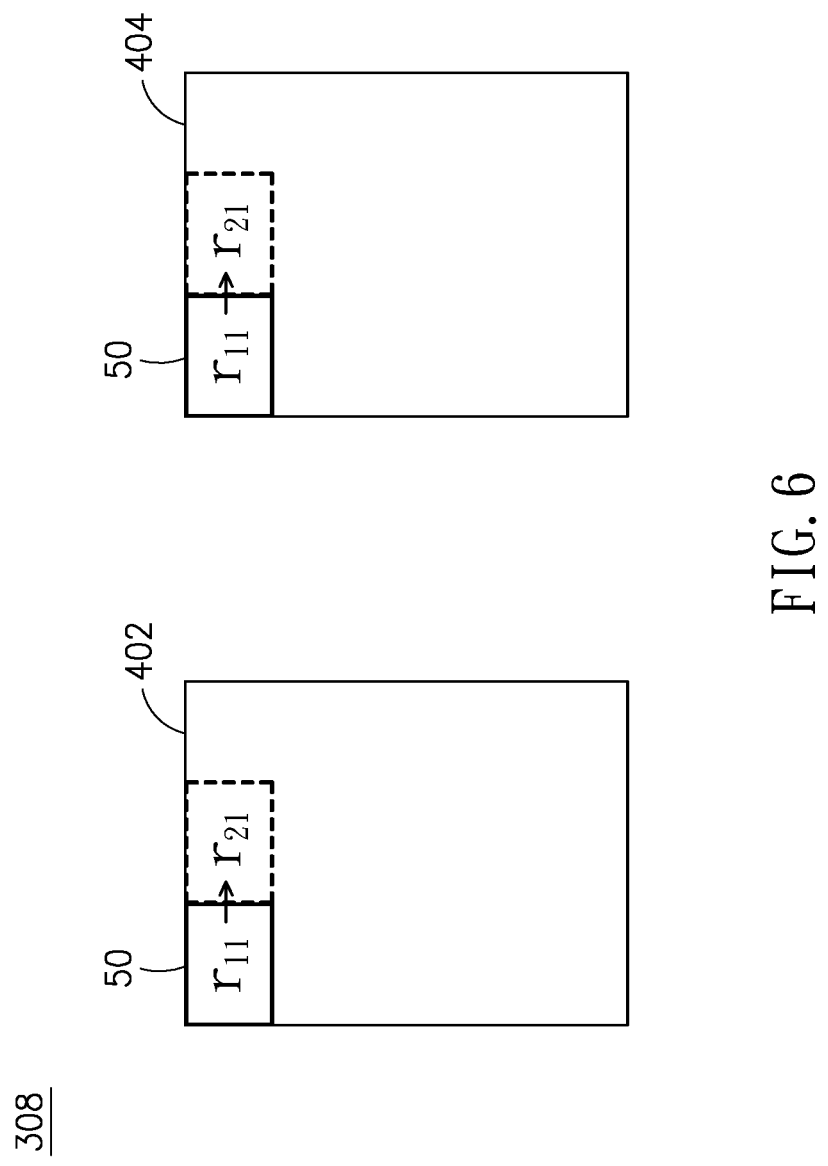
FIG. 6 is a schematic diagram showing a sliding window mask according to an embodiment of the present disclosure.

At step S130, an overlapping image information 306 is generated by aligning the second image 304 with the first image 302 according to the first feature point group and the second feature point group. FIG. 5A is a schematic diagram showing the aligning of the second image to the first image according to an embodiment of the present disclosure. FIG. 5B is a schematic diagram showing an overlapping image information extracted FIG. 5A. In this embodiment, the aligning of the second image 304 with the first image 302 that is enabled by the use of the information alignment module 126 is enabled by the use of a random sample consensus (RANSAC) algorithm with affine mapping, as shown in FIG. 5A. After aligning the second image 304 with the first image 302, a correlated image area 306 of the images is detected and used as a region of interest (ROI) for generating the overlapping image information 308 accordingly, as shown in FIG. 5B, whereas the overlapping image information 308 includes a first matching image 402 that is corresponding to the first image 302, and a second matching image 404, that is corresponding to the second image, as shown in FIG. 6. FIG. 6 is a schematic diagram showing a sliding window mask according to an embodiment of the present disclosure. For clarification, the images shown in FIG. 6 is simply provided for separating the first matching image 402 from overlapping with the second matching image 404 in the overlapping image information 308, whereas in reality, the first matching image 402 is overlapped with the second matching image 404.

At step S140, a sliding window mask 50 is used for sequentially extracting corresponding window areas from the first matching image 402 and the second matching image 404 in the overlapping image information 308, while calculating an image difference ratio for each of the window areas according to the ratio between the number of matching points and the number of unmatched points in the corresponding window areas of the first and the second matching images 402, 404, In an embodiment, the sliding window mask 50 used in the difference comparison module 142 is formed in a rectangular shape, but it is not limited thereby and can be in any shape according to actual requirement. By the sequential extraction of the sliding window mask 50 that are performed respectively on the first matching image 402 and the second matching image 404 for obtaining corresponding window areas $r_{xy}$, the first matching image 402 and the second matching image 404 are partitioned and segmented into a plurality of the window areas $r_{xy}$, whereas x and y represents respectively the horizontal coordinate and the vertical coordinate in a coordinate system.

In this embodiment, any two neighboring window areas that are defined by two continue movements of the sliding window mask 50 are not overlapped with each other, so that there is no overlapping between window areas $r_{xy}$. However, the present disclosure is not limited thereby, and thus in other embodiments, there are partial overlapping between any two neighboring window areas that are defined by two continue movements of the sliding window mask 50, i.e. there can be overlapping between window areas $r_{xy}$.

In an embodiment, the image difference ratio $f(r_{xy})$ is represented by the following formula:

$$f(r_{xy}) = \frac{n_i + n_j}{(n_i + M_i) + (n_j + M_j)}; \quad (1)$$

$$f(r_{xy}) = \frac{n_i \times n_j}{(n_i + M_i) \times (n_j + M_j)}; \quad (2)$$

wherein, $0 \leq f(r_{xy}) \leq 1$

In the formula (1) and formula (2), $n_i$ is the number of unmatched points in the $i^{th}$ image; $n_j$ is the number of unmatched points in the $j^{th}$ image; $M_i$ is the number of matched points in the $i^{th}$ image; $M_j$ is the number of matched points in the $j^{th}$ image; and the $i^{th}$ image and the $j^{th}$ image are images of the same object that are captured at different time points. In this embodiment, the first matching image 402 is defined to be the $i^{th}$ image, and the second matching image 404 is defined to be the $j^{th}$ image. In the present disclosure, the image difference ratio $f(r_{xy})$ is the ratio between the number of matching points and the number of unmatched points, as shown in the formula (1) and formula (2), but it is not limited thereby.

In this embodiment, the sliding window mask 50 is enabled to move simultaneously in the first and the second matching images 402, 404, while extracting corresponding window areas $r_{xy}$ respectively from the first matching image 402 and the second matching image 404 in each movement. In FIG. 6, assuming the initial position of the sliding window mask 50 is the $r_{11}$ window areas in the first matching image 402 and the second matching image 404, first an calculation is enabled to obtain the ratio between the number of matching points and the number of unmatched points in the window areas $r_{11}$. That is, by detecting the first feature point group in the first matching image 402 and the second feature point group in the second matching image 404 for matching the first feature point group with the second feature point group so as to obtain the number of matching points and the number of unmatched points; and thereby, the ratio between the number of matching points and the number of unmatched points can be obtained and used in the formula (1) and the formula (2) for obtaining an image difference ratio $f(r_{11})$ of the window area $r_{11}$.

Then, the sliding window mask 50 is moved from the window area $r_{11}$ to the neighboring window are $r_{21}$. Similarly, an image difference ratio $f(r_{21})$ of the window area $r_{21}$ can be obtained. In this embodiment, there is no overlapping between the window area $r_{11}$ and the window are $r_{21}$. However, in another embodiment that is not provided in this description, there can be overlap between the window area $r_{11}$ and the window are $r_{21}$.

In an embodiment, when formula (1) is used for defining the image difference ratio $f(r_{xy})$, the image difference ratio $f(r_{11})$ of the window area $r_{11}$ is 0, which indicates that all the feature points detected in the first matching image 402 match entirely to those detected in the second matching image 404. Thus, it can conclude that the difference between the window area $r_{11}$ of the first matching image 402 and the window area $r_{11}$ of the second matching image 404 is almost neglectable. Accordingly, by the use of the step S140, the image difference ratios $f(r_{xy})$ for all the window areas $r_{xy}$ defined in the overlapping image information 308 can be obtained and used for determining the variation between the first matching image 402 and the second matching image 404 for assisting physicians to do medical diagnosis.

At the step S150, a process for clustering the connectivity of the window areas in the overlapping image information is enabled according to the image difference ratio of each of the window areas.

In this embodiment, a cumulative amount of window areas $r_{xy}$ is calculated with respect to each image difference ratio $f(r_{xy})$ of the window area $r_{xy}$ in the overlapping image information 308 by the use of the cluster connection module 144.

Figure 7A:
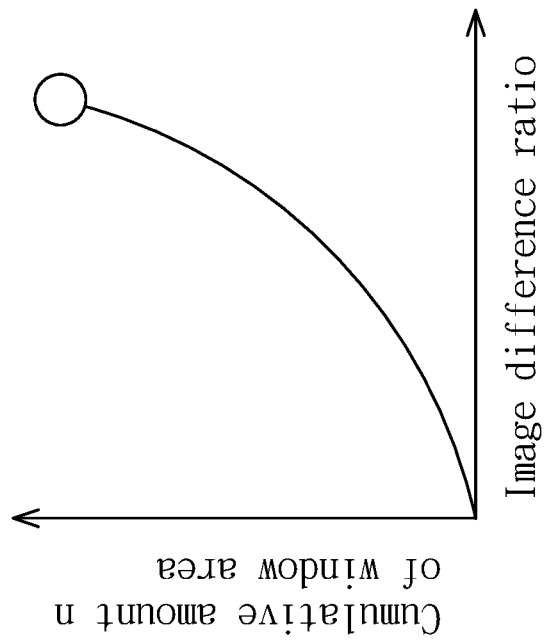
FIG. 7A is a schematic of statistic distribution between the image difference ratio and cumulative amount of window area according to an embodiment of the present disclosure.
Figure 7B:
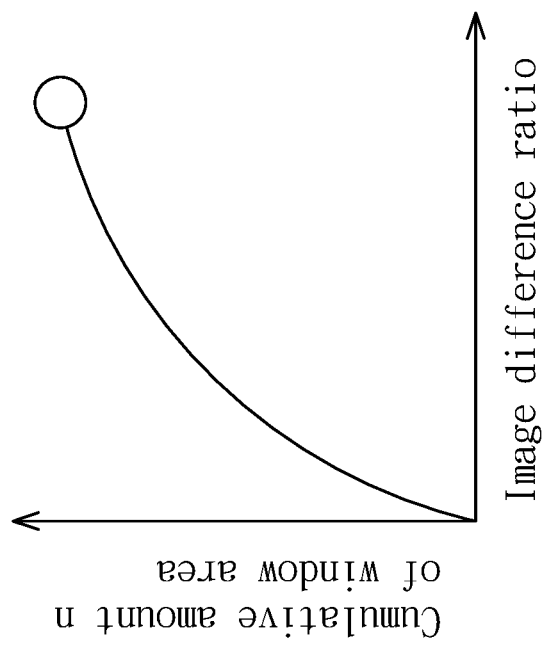
FIG. 7B is a schematic of statistic distribution between the image difference ratio and cumulative amount of window area according to another embodiment of the present disclosure.

Operationally, since the image difference ratio $f(r_{xy})$ for each window area $r_{xy}$ in the overlapping image information 308 can be obtained from the step S140, the process then will define a series of cumulative cluster intervals to be used for clustering window areas $r_{xy}$ whose corresponding image difference ratios $f(r_{xy})$ is confirming to the defining of one cumulative interval in the series of cumulative cluster intervals as the same group. For instance, as the image difference ratios $f(r_{xy})$ are values ranged between 0 and 1 and defining the series of ten cumulative cluster intervals as following: the first cumulative cluster interval is ranged between 0~0.1, the second cumulative cluster interval is ranged between 0~0.2, . . . , and the tenth cumulative cluster interval is ranged between 0~1, accordingly the window areas $r_{xy}$ can be clustered and assigned to the cluster group according to their respective image difference ratios $f(r_{xy})$, and then the cumulative amount of window areas $r_{xy}$ for each of the cumulative cluster intervals can be calculated and obtained. In this embodiment, a statistic distribution between the image difference ratio $f(r_{xy})$ and the cumulative amount of window area can be generated, whereas the statistic distribution can be represented as a histogram, a bar chart, a pie chart or a line chart. In other embodiments, the statistic distribution is represented as a table. As shown in FIG. 7A and FIG. 7B, the statistic distribution are represented as line charts, whereas the horizontal coordinate represents the image difference ratio $f(r_{xy})$ and the vertical coordinate represents the cumulative amount n of window area $r_{xy}$. As shown in FIG. 7A, with the increasing of the image difference ratio $f(r_{xy})$, the increasing of the cumulative amount n of window area $r_{xy}$ is slowing down which indicate that the region of variation is concentrating at window areas with smaller image difference ratio $f(r_{xy})$, and there is little difference between the two images. Comparing to that shown in FIG. 7B where with the increasing of the image difference ratio $f(r_{xy})$, the increasing of the cumulative amount n of window area $r_{xy}$ is rising abruptly which indicate that the region of variation is concentrating at window areas with larger image difference ratio $f(r_{xy})$, and there is a big difference between the two images.

Figures 8A, 8B:
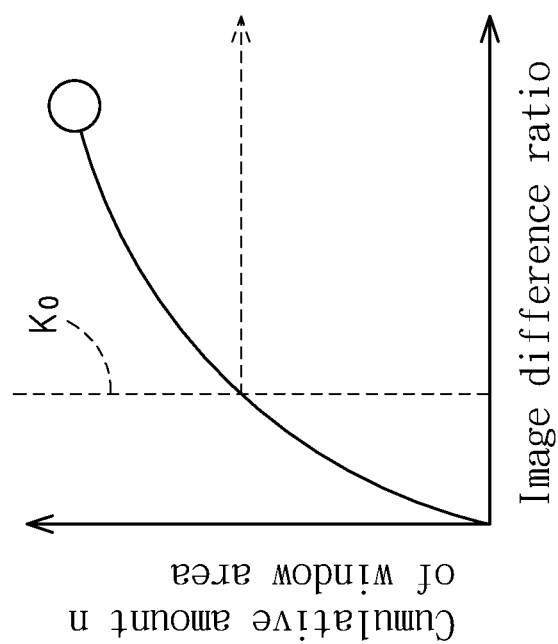
FIG. 8A is a schematic of statistic distribution using a connected component labeling method.
FIG. 8B is a schematic diagram showing an overlapping image information using a connected component labeling method according to an embodiment of the present disclosure.
Figure 8C:
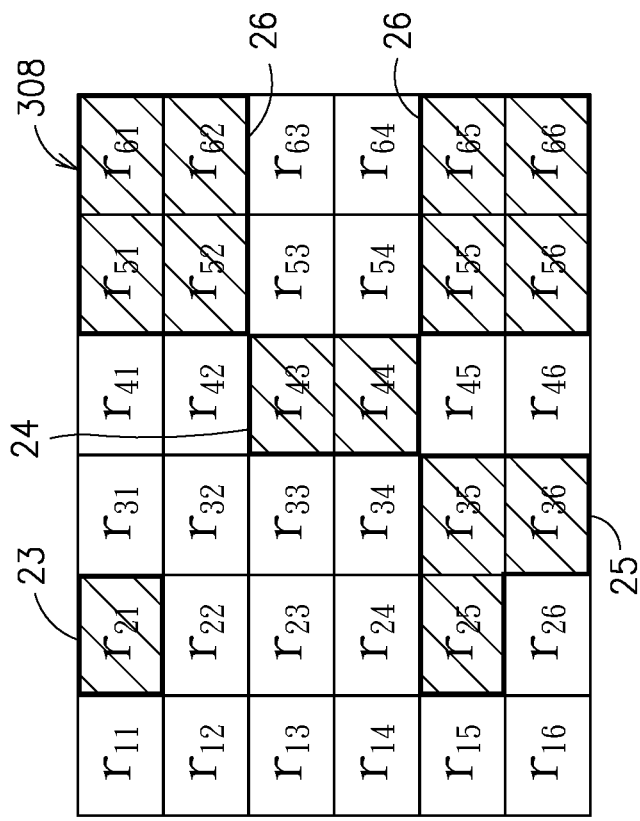
FIG. 8C is a schematic diagram showing an overlapping image information using a connected component labeling method according to another embodiment of the present disclosure.

FIG. 8A is a schematic of statistic distribution using a connected component labeling method. FIG. 8B is a schematic diagram showing an overlapping image information using a connected component labeling method according to an embodiment of the present disclosure. FIG. 8C is a schematic diagram showing an overlapping image information using a connected component labeling method according to another embodiment of the present disclosure. It is noted that the amount of window area in the overlapping image information 308 of FIG. 8B as well as the amount of window area in the overlapping image information 308 of FIG. 8C are only used for illustration, and thus the present disclosure is not limited thereby. In the statistic distribution shown in FIG. 8A, the image difference ratio $f(r_{xy})$ are scanned in a manner from small to large in value. In another embodiment, the image difference ratio $f(r_{xy})$ can be scanned in a manner from large to small in value. For instance, in an embodiment, a value $k_0$ is defined as a specific image difference ratio $f(r_{xy})$, and then a scanning is enabled on the overlapping image information 308 for locating all the window areas with image difference ratio $f(r_{xy})$ that are conforming to the specific value $k_0$ so as to label those window areas $r_{xy}$ as the selected window areas of the specific value. As the overlapping image information 308 shown in FIG. 8B, the image difference ratio $f(r_{23})$ of the window area $r_{23}$, the image difference ratio $f(r_{24})$ of the window area $r_{24}$, the image difference ratio $f(r_{31})$ of the window area $r_{31}$, and the image difference ratio $f(r_{33})$ of the window area $r_{33}$ are conforming to the specific value $k_0$, and thus the window area $r_{23}$, the window area $r_{24}$, the window area $r_{31}$, and the window area $r_{33}$ are defined as the selected window areas of the specific value. In another embodiment shown in FIG. 8C, when a specific value range k~d of the image difference ratio $f(r_{xy})$ is defined and the scanning indicates that the image difference ratio $f(r_{21})$ of the window area $r_{21}$, the image difference ratio $f(r_{51})$ of the window area $r_{51}$, the image difference ratio $f(r_{61})$ of the window area $r_{61}$, the image difference ratio $f(r_{52})$ of the window area $r_{52}$, the image difference ratio $f(r_{62})$ of the window area $r_{62}$, the image difference ratio $f(r_{43})$ of the window area $r_{43}$, the image difference ratio $f(r_{44})$ of the window area $r_{44}$, the image difference ratio $f(r_{25})$ of the window area $r_{25}$, the image difference ratio $f(r_{35})$ of the window area $r_{35}$, the image difference ratio $f(r_{36})$ of the window area $r_{36}$, the image difference ratio $f(r_{55})$ of the window area $r_{55}$, the image difference ratio $f(r_{65})$ of the window area $r_{65}$, the image difference ratio $f(r_{56})$ of the window area $r_{56}$, the image difference ratio $f(r_{66})$ of the window area $r_{66}$ are conforming to the specific value range k~d, and thus those window areas are defined as the selected window areas of the specific value. Thereafter, a detection is enabled on those selected window areas of the specific value for identifying and grouping the neighboring window areas in the selected window areas of the specific value into regions of variation. In this embodiment, a connected component labeling method is used in the detection for identifying and grouping the neighboring window areas in the selected window areas of the specific value into regions of variation, whereas the connected component labeling method can be a 8-neighbor point connected component labeling method, or a 4-neighbor point connected component labeling method.

As shown in FIG. 8B, the window area $r_{23}$, the window area $r_{24}$, and the window area $r_{33}$ are neighbors, so that they are connected to form one region of variation 20. That is, the present disclosure is able to connect individual smaller window areas according to defining of the image difference ratio into one larger region of variation. In addition, as each window area is defined by the use of the sliding window mask 50 with known area size, the total area of the region of variation can be obtained as the totality of the window areas in the region of variation. That is, as shown in FIG. 8B, the total area of the region of variation 20 is the total area of the window area $r_{23}$, the window area $r_{24}$, and the window area $r_{33}$. In FIG. 8B, the window area $r_{31}$ itself forms one individual region of area 22 as it is not connected to any other selected window areas of the specific value, and thus it is defined as a variation region of one-unit-area, whereas the variation region 22 of FIG. 8A is defined as a variation region of three-unit-area as it is the collection of three window areas. However, in other embodiments, there can be partial overlapping in the neighboring window areas in each movement of the sliding window mask 50, so that the total area of the variation region should be the totality of the neighboring window area after subtracting the overlapping area.

As shown in FIG. 8C, the window area $r_{21}$, indicating as the region 23, is a stand along area that is not connected to other selected area and thus is assigned as a variation region of one-unit-area; the window area $r_{43}$ and the window area $r_{44}$ are connected into a variation region 24 of two-unit-area; the window area $r_{25}$, the window area $r_{35}$ and the window area $r_{36}$ are connected into a variation region 25 of three-unit-area; the window area $r_{51}$, the window area $r_{52}$, the window area $r_{61}$, and the window area $r_{62}$ are connected into a variation region 26 of four-unit-area; and similarly the window area $r_{55}$ and the window area $r_{56}$, the window area $r_{65}$, and the window area $r_{66}$ are connected into another variation region 26 of four-unit-area.

At step S150, the connectivity of the window areas in the overlapping image information is clustered according to the image difference ratio of each of the window areas; and then the flow proceeds to step s160, At step S160, the region of variation on the overlapping image information is identified and labeled. In this embodiment, the output device 16 is used for outputting an overlapping image information 308 and provided for assisting physicians or medical personnel to do diagnosis by labeling a specific value b to the variation regions.

Figure 9A:
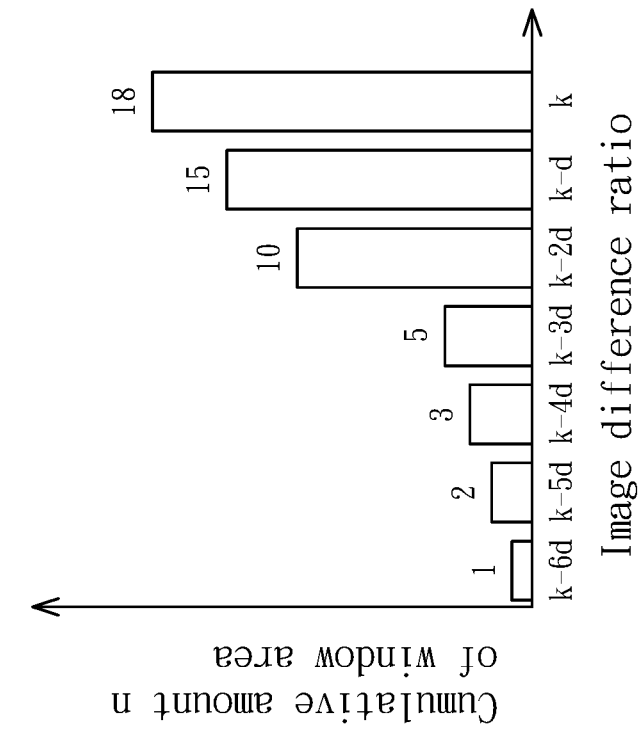
FIG. 9A is a schematic of statistic distribution between the image difference ratio and cumulative amount in window area according to an embodiment of the present disclosure.

FIG. 9A is a schematic of statistic distribution between the image difference ratio and cumulative amount in window area according to an embodiment of the present disclosure. The statistic distribution shown in FIG. 9A is a histogram, in which the horizontal coordinate represents the image difference ratio $f(r_{xy})$ and the vertical coordinate represents the cumulative amount n of window area $r_{xy}$. In other embodiments, the statistic distribution can be represented using a table. Similar to the forgoing description, the process then will define a series of cumulative cluster intervals d to be used for clustering window areas $r_{xy}$ whose corresponding image difference ratios $f(r_{xy})$ is confirming to the defining of one cumulative interval in the series of cumulative cluster intervals as the same group, while counting the total amount of the window areas $r_{xy}$ of the same group as its cumulative amount n. In the embodiment shown in FIG. 9A, the bar at the image difference ratios $f(r_{xy})$ of k represents the window areas $r_{xy}$ whose image difference ratios $f(r_{xy})$ is ranged between 0~k and the cumulative amount n of those window areas $r_{xy}$ is 18; the bar at the image difference ratios $f(r_{xy})$ of k–d represents the window areas $r_{xy}$ whose image difference ratios $f(r_{xy})$ is ranged between 0~k–d and the cumulative amount n of those window areas $r_{xy}$ is 15; the bar at the image difference ratios $f(r_{xy})$ of k–2d represents the window areas $r_{xy}$ whose image difference ratios $f(r_{xy})$ is ranged between 0~k–2d and the cumulative amount n of those window areas $r_{xy}$ is 10; the bar at the image difference ratios $f(r_{xy})$ of k–3d represents the window areas $r_{xy}$ whose image difference ratios $f(r_{xy})$ is ranged between 0~k–3d and the cumulative amount n of those window areas $r_{xy}$ is 5; the bar at the image difference ratios $f(r_{xy})$ of k–4d represents the window areas $r_{xy}$ whose image difference ratios $f(r_{xy})$ is ranged between 0~k–4d and the cumulative amount n of those window areas $r_{xy}$ is 3; the bar at the image difference ratios $f(r_{xy})$ of k–5d represents the window areas $r_{xy}$ whose image difference ratios $f(r_{xy})$ is ranged between 0~k–5d and the cumulative amount n of those window areas $r_{xy}$ is 2; and the bar at the image difference ratios $f(r_{xy})$ of k−6d represents the window areas $r_{xy}$ whose image difference ratios $f(r_{xy})$ is ranged between 0~k−6d and the cumulative amount n of those window areas $r_{xy}$ is 1.

Figure 9C:
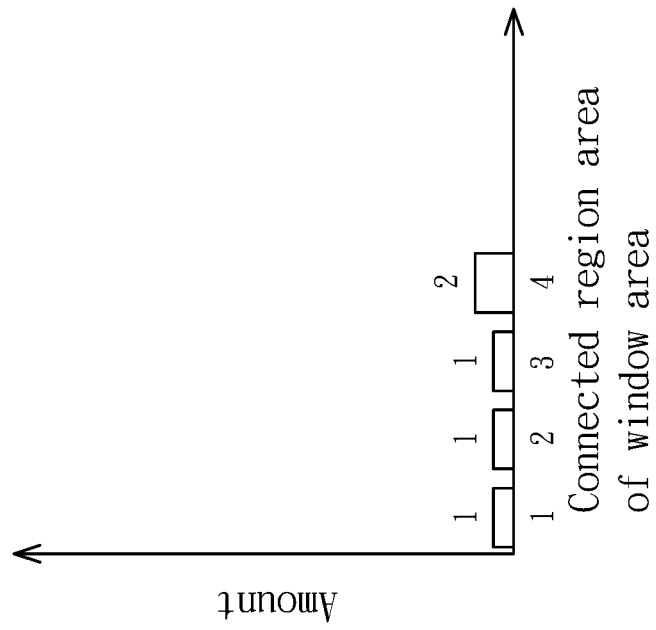
FIG. 9C is a schematic of statistic distribution of connected region area in window area.
Figure 9B:
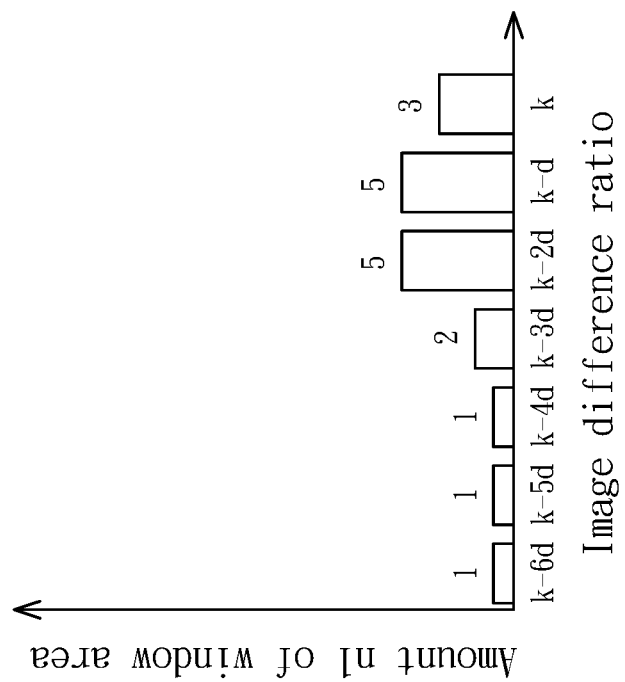
FIG. 9B is a schematic of statistic distribution between the image difference ratio and the amount in window area according to an embodiment of the present disclosure.

From the cumulative amount n of those window areas $r_{xy}$ shown in FIG. 9A, it is able to known the amount of window areas for each of the image difference ratio $f(r_{xy})$. FIG. 9B is a schematic of statistic distribution between the image difference ratio and the amount in window area according to an embodiment of the present disclosure. The static distribution of FIG. 9B is also a histogram, which is similar to that shown in FIG. 9A but is not limited thereby. Similarly, the statistic distribution shown in FIG. 9B is a histogram, in which the horizontal coordinate represents the image difference ratio $f(r_{xy})$ and the vertical coordinate represents the amount n1 of window area $r_{xy}$. In the embodiment shown in FIG. 9B, a cumulative cluster interval d is used for clustering the window areas. As shown in FIG. 9B, the bar at the image difference ratios $f(r_{xy})$ of k−6d represents the window areas $r_{xy}$ whose image difference ratios $f(r_{xy})$ is ranged between 0~k−6d and the amount n1 of those window areas $r_{xy}$ is 1, whereas in FIG. 9A, the bar at the image difference ratios $f(r_{xy})$ of k−5d represents the window areas $r_{xy}$ whose image difference ratios $f(r_x)$ is ranged between 0~k−5d and the cumulative amount n of those window areas $r_{xy}$ is 2, therefore, it can conclude that after subtracting the one window area with image difference ration of k−6d, the amount n1 of the window area with image difference ratios $f(r_{xy})$ is ranged between k−5d~k−6d is 1, and therefore, in FIG. 9B, the bar at the. Similarly, it can conclude that the bar at the image difference ratios $f(r_{xy})$ of k−5d represents the amount n1 of those window areas $r_{xy}$ with image difference ratios $f(r_{xy})$ of k−5d is 1. Consequently, in FIG. 9B, the amount n1 of those window areas $r_{xy}$ with image difference ratios $f(r_{xy})$ of k−4d is 1; the amount n1 of those window areas $r_{xy}$ with image difference ratios $f(r_{xy})$ of k−3d is 2; the amount n1 of those window areas $r_{xy}$ with image difference ratios $f(r_{xy})$ of k−2d is 5; the amount n1 of those window areas $r_{xy}$ with image difference ratios $f(r_{xy})$ of k−d is 5; and the amount n1 of those window areas $r_{xy}$ with image difference ratios $f(r_{xy})$ of k is 3. In other word, the region with maximum variation is the region with image difference ratios $f(r_{xy})$ of k, and the amount n1 of those window areas $r_{xy}$ with image difference ratios $f(r_{xy})$ ranged between k−d~k is 3; while the region with minimum variation is the region with image difference ratios $f(r_{xy})$ of k−6d, and the amount n1 of those window areas $r_{xy}$ with image difference ratios $f(r_{xy})$ ranged between 0~k−6d is 1.

Thereafter, a connected component labeling algorithm is used by the defining of a specific value b, that is, when a physician input a value b, he/she is intended to locate b regions of variation that are most obvious in the overlapping image information. In an embodiment, if the specific value b is 3, and in FIG. 9B where the amount n1 of those window areas $r_{xy}$ with image difference ratios $f(r_{xy})$ of k is 3, by that the required amount of variation regions are located and labeled for providing the variation regions to the physician to do diagnosis.

In another embodiment, if the specific value b is 7, and in FIG. 9B where the amount n1 of those window areas $r_{xy}$ with image difference ratios $f(r_{xy})$ of k is 3 and the amount n1 of those window areas $r_{xy}$ with image difference ratios $f(r_{xy})$ of k−d is 5, therefore the there are 8 window areas to be located that is more than the specific amount of 7. Please refer to FIG. 9C, which is a schematic of statistic distribution of connected region area in window area. In FIG. 9C, the horizontal coordinate represents the connected region area, which are one-unit-area, two-unit-area, three-unit-area and for-unit-area from small to large, and the vertical coordinate represents the amount of the corresponding window areas of different sizes. It is noted that the histogram shown in FIG. 9C represents the window area with image difference ratios $f(r_{xy})$ of k−d of FIG. 8C. In FIG. 9C using the window area with image difference ratios $f(r_{xy})$ of k−d, the window area $r_{21}$, indicating as the region 23, is a stand along area that is not connected to other selected area and thus is assigned as a variation region of one-unit-area, and three is only one variation region of one-unit-area; similarly, there is one variation area of two-unit-area 24, which is a connected region of the window area $r_{43}$ and the window area $r_{44}$; there is one variation area of three-unit-area 25, which is a connected region of the window area $r_{25}$, the window area $r_{35}$ and the window area $r_{36}$; and there are two variation area of four-unit-area 26, which are respectively a region of; the window area $r_{51}$, the window area $r_{52}$, the window area $r_{61}$, and the window area $r_{62}$, and a region of the window area $r_{55}$ and the window area $r_{56}$, the window area $r_{65}$, and the window area $r_{66}$. In this embodiment, regardless the variation region contains only one window area or it is an assembly of multiple window areas, the identified variation regions are ordered according to their size, while the four largest variation regions are selected. That is, in this embodiment, the two variation area of four-unit-area 26 are selected first, and then the variation area of three-unit-area 25, the variation area of two-unit-area 24 are selected following.

To sum up, the medical comparison method and system of the present disclosure are capable of rapidly comparing medical images of a specific area in a patient that are taken at different time according to the image difference ratio so as to locate a region of variation from the medical images, by that physicians not only can be relieved from the time-consuming and labor-intensive task of having to manually search and find all the differences between retinal images that are taken at different time, but also from possible misdiagnosis caused by human error. Moreover, physicians are enabled to make a more objective valuation to determine whether or not the region of variation is an indication of deterioration for assisting the physicians to arrange corresponding tracking procedures.

By the image difference ratios obtained in the present disclosure, the degree of matching between two images of the same target area can be evaluated and determined, which can be performed without being limited by the differences in imaging angle, the use of light source, luminance and parameter configuration between different retinal imaging processes in each imaging.

In addition, by the image difference ratios obtained in the present disclosure for defining the connectivity of the window areas, window areas can be clustered and connected so as to be used for labeling variation region according to a specific label value, and thus the label variation regions can be provided to a physician to be diagnosis.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A medical image comparison method, comprising the steps of:
   obtaining a plurality of images of a body at different time points, while allowing the plural images to include a first image captured at a first time point and a second image captured at a second time point;
   obtaining a first feature point group by detecting feature points in the first image, while obtaining a second feature point group by detecting feature points in the second image;
   enabling an overlapping image information to be generated by aligning the second image with the first image according to the first feature point group and the second feature point group, while allowing the overlapping image information to include a first matching image corresponding to the first image and a second matching image corresponding to the second image; and
   sequentially extracting corresponding window areas from the first matching image and the second matching image in the overlapping image information respectively by the use of a sliding window mask, while calculating an image difference ratio for each of the window areas according to the ratio between the number of matching points and the number of unmatched points in the corresponding window areas of the first and the second matching images.

2. The method of claim 1, further comprising the step of:
   clustering the connectivity of the window areas in the overlapping image information according to the image difference ratio of each of the window areas.

3. The method of claim 2, wherein the clustering of the connectivity of the window areas in the overlapping image information further comprises the step of:
   calculating a cumulative amount of window areas according to the corresponding image difference ratio.

4. The method of claim 3, wherein the clustering of the connectivity of the window areas in the overlapping image information further comprises the step of:
   labeling the window areas with image difference ratios that are conforming to a specific value as a specific window area; and
   determining whether the labeled window areas are neighboring to one another, while connecting the neighboring labeled window areas into a region of variation.

5. The method of claim 4, further comprising the step of:
   identifying and labeling the region of variation on the overlapping image information.

6. The method of claim 1, wherein the obtaining of the first feature point group of the first image and the second feature point group of the second image further comprises the step of:
   using a scale invariant feature transform (SIFT) algorithm and a speeded-up robust features (SURF) algorithm to obtain the first feature point group of the first image and the second feature point group of the second image.

7. The method of claim 1, wherein the aligning of the second image with the first image is enabled by the use of a random sample consensus (RANSAC) algorithm with affine mapping.

8. The method of claim 1, wherein the use of the sliding window mask further comprises the step of:
   partitioning and segmenting the first and the second images into a plurality of the window areas.

9. The method of claim 8, wherein the window areas is arranged in a manner selected from the group consisting of: the window areas are arranged for allowing partial overlapping area against one another, and the window areas are arranged without overlapping.

10. A medical image comparison system, comprising:
    an image processing device, further comprising:
    an image capturing module, for obtaining a plurality of images of a body at different time points, while allowing the plural images to include a first image captured at a first time point and a second image captured at a second time point;
    a feature extracting module, coupling to the image capturing module, for obtaining a first feature point group by detecting feature points in the first image, while obtaining a second feature point group by detecting feature points in the second image; and
    an information alignment module, coupling to the feature extracting module, for aligning the second image with the first image according to the first feature point group and the second feature point group so as to generate an overlapping image information, while enabling the overlapping image information to include a first matching image corresponding to the first image and a second matching image corresponding to the second image; and
    an image calculation device, coupling to the image processing device, further comprises: a difference comparison module, provided for sequentially extracting corresponding window areas from the first matching image and the second matching image in the overlapping image information respectively by the use of a sliding window mask, while calculating an image difference ratio for each of the window areas according to the ratio between the number of matching points and the number of unmatched points in the corresponding window areas of the first and the second matching images.

11. The system of claim 10, further comprising:
    a cluster connection module, coupling to the difference comparison module, for clustering the connectivity of the window areas in the overlapping image information according to the image difference ratio of each of the window areas.

12. The system of claim 11, further comprising:
    an image labeling module, coupling to the cluster connection module, for labeling a region of variation on the overlapping image information.

13. The system of claim 12, further comprising:
    an output device, coupling to the image labeling module, for outputting the labeled region of variation of the overlapping image information.

14. The system of claim 10, wherein the feature extracting module uses a scale invariant feature transform (SIFT) algorithm and a speeded-up robust features (SURF) algorithm to obtain the first feature point group of the first image and the second feature point group of the second image.

15. The system of claim 10, wherein the information alignment module uses a random sample consensus (RANSAC) algorithm with affine mapping to align the second image with the first image.

* * * * *